United States Patent [19]

Zhao

[11] Patent Number: 5,641,680
[45] Date of Patent: Jun. 24, 1997

[54] GENE TRANSFER APPARATUS AND METHOD FOR USING THE SAME

[76] Inventor: Xi Zhao, 16336 W. La Chiquita Ave., Los Gatos, Calif. 95032

[21] Appl. No.: 337,862

[22] Filed: Nov. 14, 1994

[51] Int. Cl.$^6$ .............. C12N 15/00; C12N 5/00; A61K 42/00
[52] U.S. Cl. ............... 435/285.2; 435/172.3; 435/285.1; 435/289.1; 435/320.1; 514/44
[58] Field of Search ............... 514/44; 424/93.21; 435/172.3, 320.1, 240.1, 240.2, 285.2, 285

[56] References Cited

U.S. PATENT DOCUMENTS 4,663,292 5/1987 Wong et al. .............. 435/287
4,849,355 7/1989 Wong ..................... 435/172.3

OTHER PUBLICATIONS

Toneguzzo et al., Stable expression of selectable genes . . . , Proc. Natl. Acad. Sci, vol. 83, pp. 3496–3499, May 1986.
Potter, H., Anal. Biochem., Electroporation in Biology, vol. 174, 361–373 (1988).
Marshall, Science, 269, 1995, 1050–1055.
Miller et al., FASEB J., 9, 1995, 190–199.
Culver et al., TIG, 10(5), 1994, 174–178.
Hodgson, Exp. Opin. Ther. Pat., 5(5), 1995, 459–468.
Experimental Hematology, vol. 18, 1990, Keating, et al., "Effect of Different Promoters on Expression of Genes Introduced Into Hematopoietic and Marrow Stromal Cells by Science, vol. 269, Aug. 1995, Marshall, Gene Therapy's Growing Pains", pp. 1050–1055.
PCT International Search Report, PCT/US95/14031, Feb. 14, 1996.

*Primary Examiner*—Jacqueline M. Stone
*Assistant Examiner*—Andrew Milne
*Attorney, Agent, or Firm*—Blakely, Sokoloff, Taylor & Zafman

[57] ABSTRACT

A method and apparatus for performing gene therapy treatment. The method comprises selecting a genetic vector, introducing a genetic material into the genetic vector, combining the modified genetic vector with an electronic pulse delivery buffer solution with cells from an organism, and performing electronic pulse delivery on the combination in a reaction chamber to produce transformed cells, and placing the transformed cells into an organism. The reaction chamber includes a main chamber having a first substantially flat face and which holds a combination of the genetic material, a plurality of cells from the organism and an electronic pulse delivery buffer solution. The reaction chamber also includes a first electrode which has a second substantially flat face which is disposed opposite to and proximate to the first substantially flat face. The first electrode is coupled to receive electronic pulses to perform electronic pulse delivery of the genetic material into at least some of the plurality of cells.

4 Claims, 14 Drawing Sheets

A = AMPLITUDE
Cy = CYCLE
NP = NUMBER OF PULSES
$T_P$ = PULSE (p) TIME
$T_B$ = BURST TIME = $T_A + T_R$
$T_A$ = ACTION TIME = NP × $T_P$
$T_R$ = RELAXATION TIME
D = DISTANCE BETWEEN THE ANODE AND MOLECULE-CELL OR CELL-CELL MIXTURE

GENE TRANSFER APPARATUS AND METHOD FOR USING THE SAME

FIELD OF THE INVENTION

The present invention relates to gene therapy for an organism and more particularly to gene therapy for an organism using electronic pulse delivery to cause the integration of genetic material into target cells which are delivered into the organism.

BACKGROUND OF THE INVENTION

It has been a general objective in the field of biotechnology to develop gene therapy protocols in order to cure and/or treat diseases and illnesses which are at least partially caused by genetic disorders or may be treated with gene therapy protocols. For example, there exists a gene therapy protocol for the correction of adenosine deaminase (ADA) deficiency. See W. French Anderson, *Science*, volume 256, pages 808–813 (May 8, 1992). Many procedures for gene therapy must deal with the issue of delivering the new genetic material ("gene") into the target cells which are delivered into the organism for which gene therapy is to be carried out.

In the prior art, there are numerous methods for causing this delivery, such as the use of liposomes, microinjection, infectious viral vectors, and calcium phosphate mediated DNA transfer. The use of liposomes, while somewhat popular, requires a considerable effort in designing a liposome carrier for genetic material and is often not efficient in effecting a transfer of genetic material any may often clot lung capillary vessels. Microinjection is a very tedious and slow process given that each cell must be injected while observing the cell in a light microscope. The predominant approach currently for causing the transfer of new genetic material into the recipient cells for delivery into the organism for which gene therapy is intended has been the use of viral vectors which are designed to infect and transform a target cell from the organism, which target cell, after transformation, is placed back into the organism typically by implantation into the organism or injection into a circulatory system of the organism.

While most of gene therapy under investigation today, particularly gene therapy for use in humans, involves the use of somatic cells as the target cell, gene therapy has been considered for use in germ cells and in stem cells, such as hematopoietic stem cells, as the target cell. The selection of a particular viral vector will depend on the particular target cell and thus there is considerable specificity required in determining the viral vector relative to the particular target cell. That is, the selection of the viral vector will depend on the selection of the target cell and there are no general or simple rules in the case of selecting viral vectors for use with particular target cells for use in gene therapy. Thus, research is continuing on various improved methods for delivering genetic material into target cells for use in gene therapy.

One technique in the prior art for delivery of genetic material into cells has been the use of electronic pulse delivery systems and procedures such as those described in U.S. Pat. No. 4,849,355 and U.S. Pat. No. 4,663,292. While these procedures and techniques have been utilized to transfer macromolecules into cells, they have not been used for the purpose of gene therapy. The prior art electronic pulse delivery systems utilized reaction chambers with pointed electrodes in order to maximize the electric field near the electrodes and utilized reaction chambers where at least one electrode was in contact with the solution containing the cells. This has been found to not be as advantageous as certain improved reaction chambers, provided by the present invention, with substantially flat electrodes and where the electrodes are physically isolated (and electrically insulated) from the solution containing the cells.

Thus, it is desirable to provide an improved technique for delivery of genetic material into cells for the purpose of performing gene therapy treatment on the organism, typically by placing transformed cells back into the organism.

SUMMARY OF THE INVENTION

A method and apparatus for performing gene therapy treatment on an organism is disclosed. In one typical embodiment according to the invention, the gene therapy uses electronic pulse delivery to introduce genetic material into cells which have been isolated from an organism for the purpose of transforming those cells and then placing those cells back into the organism to perform gene therapy on the organism.

In a typical embodiment, the method includes the steps of selecting a particular genetic vector (e.g. a plasmid) and inserting the desired genetic material into the genetic vector to produce a modified genetic vector. This modified genetic vector is then combined with the plurality of cells isolated from the organism in an electronic pulse delivery buffer solution. The combination of the modified genetic vector and the plurality of cells from the organism in the buffer solution is then subjected to electronic pulse delivery procedures by applying an electric field across a reaction chamber, which typically has at least one substantially flat surface disposed opposite to and proximate to an electrode which is used to apply the electric field. The electric field is usually pulsed repeatedly over short periods of time, and the pulses are usually grouped into a cycle and multiple cycles are usually applied in the electronic pulse delivery procedure. The electrodes are typically isolated (physically and electrically insulated) from the solution containing the cells and the modified genetic vector.

After electronic pulse delivery (EPD) a plurality of the cells from the organism become transformed cells and they are then typically placed back into the organism in order to perform gene therapy. The transformed cells typically produce a gene product which is the expression of the genetic material which has been inserted into the genome of the transformed cells. If the transformed cells are stem cells, they will typically reproduce in the organism and the treatment will often be permanent as the stem cells continue to renew, multiply, and differentiate into mature, developed cells of the organism.

In one embodiment, the stem cells are hematopoietic stem cells. These stem cells are isolated from a particular organism (e.g. a human) using known techniques and then the isolated hematopoietic stem cells are combined with the electronic pulse delivery buffer solution and the desired genetic material which is to be inserted into the genome of these stem cells. The combination of these stem cells with the genetic material in the electronic pulse delivery buffer solution is placed in a reaction chamber in order to perform an electronic pulse delivery. While various reaction chambers may be used in this circumstance, typically, the reaction chamber will have one substantially flat surface or face which is disposed opposite to and proximate to a substantially flat plate electrode. The substantially flat plate electrode is electrically insulated and physically isolated from the solution such that it does not contact the solution and does not allow the conduction of a current directly into the solution. The electronic pulse delivery procedure is applied to the combination to produce transformed hematopoietic stem cells which are then typically injected back into the patient or organism for the purpose of providing gene therapy for the organism. Often, it is desirable to verify that the hematopoietic stem cells have been transformed using known procedures for analyzing the genome of the hematopoietic stem cells. For example, the cells after EPD may have their DNA extracted, cleaved with restriction endonucleases and then the resulting fragments run by electrophoresis through an agarose gel along with similar restriction fragments from the genetic material in order to identify that the desired gene fragments have been inserted into the genome of these stem cells.

Various EPD reaction chambers are described, including one having a main chamber with a first and second substantially flat faces. This main chamber also includes an input/output port such that the combination of the EPD buffer solution, the target cells desired to be transformed and the genetic material is placed into the main chamber through the input port, and after the EPD procedure is finished the solution and the target cells are removed from the chamber through an output port either in a continuous operation or in a batch operation. The solution may be introduced and removed from the chamber by a peristaltic pump. This reaction chamber also includes a first electrode having a third substantially flat face which is disposed opposite to and proximate to the first substantially flat face. There is a second electrode having a fourth substantially flat face which is disposed opposite to and proximate to the second substantially flat face, and the first and second electrodes are coupled to receive the electronic pulses which are used during the electronic pulse delivery procedure to create a pulsing electric field around the reaction chamber. The main chamber and its ports and connecting tubes are kept sterile before and during the EPD procedure; typically, these ports are obtained in a sterile condition and disposed of after an EPD procedure and a new set of these parts (e.g. input and output tubes and a reaction chamber all in sterile condition) is used for the next EPD procedure in the EPD reactor.

BRIEF DESCRIPTION OF THE DRAWINGS

FIG. 6b shows further aspects of an embodiment similar to that shown in FIG. 6a.

FIG. 7b and 7c show an embodiment similar to that shown in FIG. 7a.

FIG. 8b shows an embodiment similar to that shown in FIG. 8a.

DETAILED DESCRIPTION OF THE PRESENT INVENTION

The present invention is described in conjunction with various figures and examples presented in the text of this specification. As part of the examples, numerous details such as particular genetic vectors (e.g. certain plasmids), certain target cells (e.g. hematopoietic stem cells), certain genetic material, certain electronic pulse delivery (EPD) buffer solutions and EPD protocols, and certain EPD reactors with their corresponding reaction chambers are described. It will be appreciated by those in the art that the invention may be practiced with other examples which have not been described, such as other types of plasmids, other types of target cells, modified reaction chambers and EPD protocols.

Figure 1:
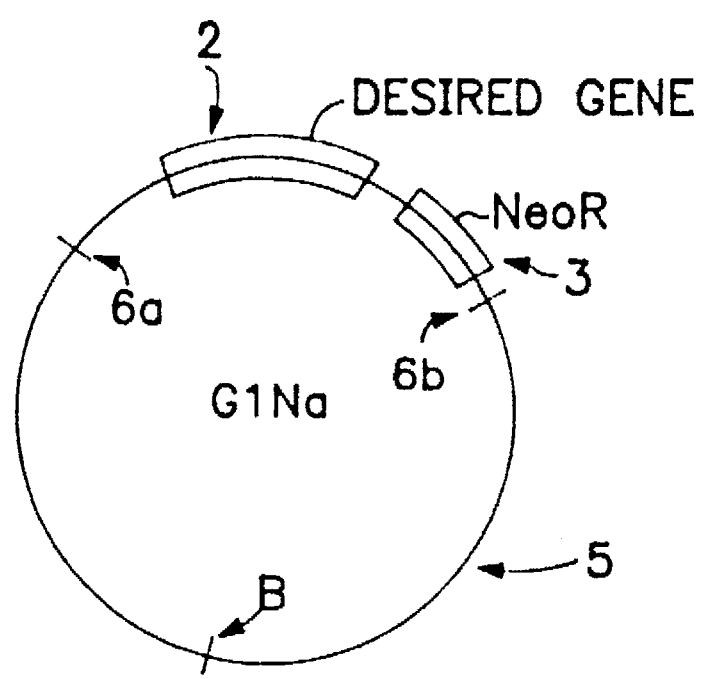
FIG. 1 shows a particular genetic vector which may be used with the present invention.

One example of the present invention will now be described while referring to FIG. 2. In the initial step shown in FIG. 2, a particular genetic vector, such as a particular plasmid, is selected. FIG. 1 shows an example of the G1Na plasmid 5 having a desired gene 2 and a marker gene 3 which is the neomycin resistant gene NeoR. The desired gene 2 and the NeoR gene 3 have been inserted at a unique restriction site 6 into the plasmid 5 using conventional recombinant DNA technology using a restriction endonuclease. For example, restriction site 6 (in the plasmid before inserting the desired gene) may be the Sac I site. The plasmids are typically selected such that there is a unique restriction site, such as restriction site 8 of FIG. 1, which may be used to linearize the plasmid. There is also typically a unique restriction site such as restriction site 6 (shown as two sites after the insertion of the desired gene and the NeoR gene) in FIG. 1. It will be appreciated that the desired gene 2 typically includes a normal complement of controlling fragments ("regulators") such as a promoter region which is upstream from the desired gene, enhancer or other regulatory elements(s). The marker gene 3 would typically be present only when verifying experimentally the gene therapy protocol rather than an actual protocol for a patient after the protocol has been verified. That is, once the protocol for gene therapy has been established and verified such that the desired gene has been established to be integrated functionally into the genome of the target cells, then only the desired gene needs to be inserted into the genetic vector for transforming cells from the organism. While it will be appreciated that a plasmid is typically used as the genetic vector, other genetic vectors such as the viruses may be used in certain embodiments of the present invention. Examples of commercially available plasmid vectors include pTK, pADFβ, pCMVFβ, and pSV, all from CloneTech of Palo Alto, Calif.

Figure 2:
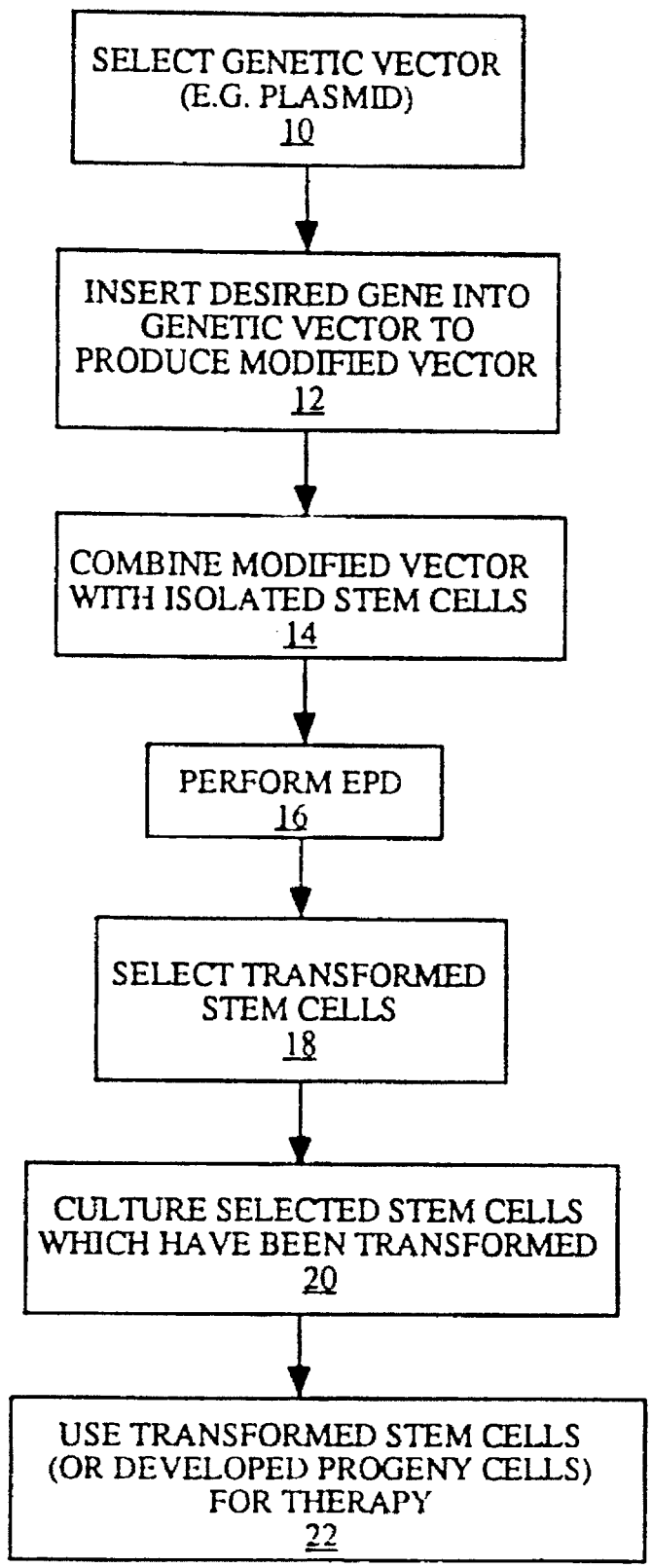
FIG. 2 shows the steps involved in a generalized example of the present invention.
Figure 9:
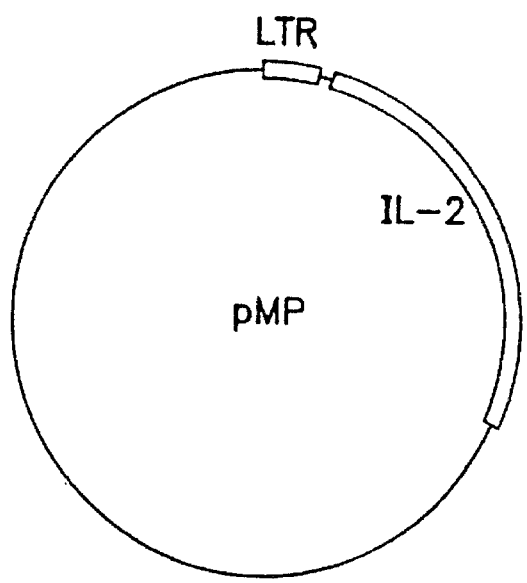
FIG. 9 shows an example of a construct map with inserted genetic material.
Figure 10:
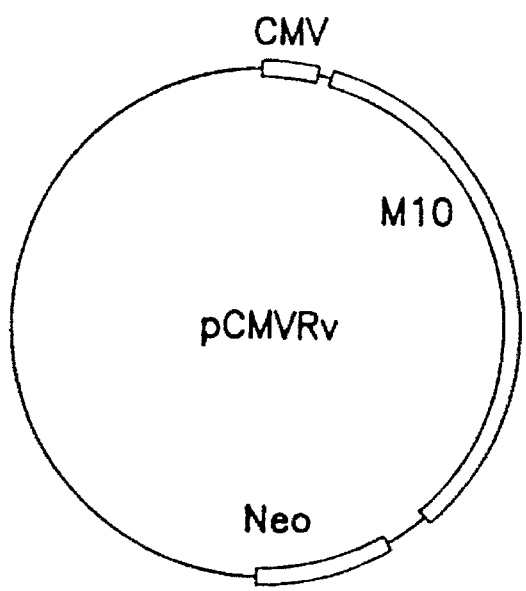
FIG. 10 shows another example of a construct map with inserted genetic material.

Once a genetic vector, such as a plasmid, has been selected as shown in step 10 of FIG. 2, then a particular desired gene is inserted, as noted above, in step 12 to produce a modified vector (sometimes referred to as a "construct") such as that shown in FIG. 1 wherein the desired gene has been integrated into the genetic vector. FIGS. 9 and 10 show several possible construct maps made from inserting desired genes into plasmid vectors.

It will be appreciated that the desired gene will depend on the particular gene therapy which in turn depends on the particular cause of the disease. It is contemplated that the typical circumstance will involve a defective gene in an organism which produces a defective protein or other defective expressed gene product (e.g. defective tRNA or defective rRNA) which is causing the disease or illness. It is also contemplated that the disease or illness may result from a missing gene which produces no expressed products at all. In these cases, gene therapy according to the present invention would use the correct gene for producing the expressed gene product, and this gene would be the desired gene which is to be inserted into a genetic vector to produce a modified genetic vector such as that shown in FIG. 1.

It is also contemplated that the desired gene or genetic material which is to be inserted may be genetic material which is not normally found in the organism's genome; antisense oligonucleotides that are designed to hybridize with certain mRNA transcripts, expressed by existing genes of the organism, are such an example. In this case, the mRNA transcripts would normally encode undesired gene products, and the antisense oligonucleotide would be designed to be an antisense copy of at least a portion of the mRNA transcript in order to prevent translation of the transcript. In this case, the gene therapy protocol seeks to inhibit the expression of the undesired gene by hybridizing with the mRNA transcript of the undesired gene. In another situation, the desired gene may be selected to increase the production of a gene product which is already being correctly expressed by an existing gene in the organism which is the subject of gene therapy. That is, the desired gene may already exist in its correct form in the organism's genome, and the gene therapy seeks to increase the production of the expressed gene product from this gene by adding another copy of the gene into target cells for delivery into the organism. Typically, it will be desired to integrate the construct into the genome of the organism although this is not always the case.

Examples of various desired genes or genetic material which may be inserted into genetic vectors are set out in the following tables.

TABLE A

GENE THERAPY
Diseases treatable with gene therapy (caused by single gene defects)

| Disease | Defective gene |
|---|---|
| Cystic fibrosis | CFTR |
| Pituitary dwarfism | hCG |
| Emphysema | ∝ 1-antitrypsin |
| Familial hypercholesterolemia | LDL receptor |
| Thalassemia major | β-globin |
| Sickle-cell anemia | β-globin |
| Hemophilia A | Factor VIII |
| Gaucher's diseases | Glucocerebrosidase |
| Phenylketonuria | Phenylalanine hydroxylase |
| SCID | Adenine Deaminase |
| SCID | Purine nucleoside phosphorylase |
| Duchenne muscular dystrophy | Dystrophin |
| Lesch-Nyhan syndrome | Hypoxanthine phosphoribosyl transferase |
| Tay-Sachs disease | Hexosaminidase |

TABLE B

GENE THERAPY
Some Acquired Diseases Amenable to Gene Therapy

| Disease | Gene Inserted |
|---|---|
| Cancer | Interleukins; TK; tumor suppresser genes |
| Cardiovacsular diseases | |
| Myocardia infarcts | tPA |
| Prevention of blood clots on cardiac stents | tPA |
| Hypercholesterolemia | LDL receptor |
| Neurdegenerative diseases | |
| Alzheimer's disease | NGF, BDNF, NT3, NT4/5 |
| Parkinsons's disease | Tyrosine hydroxylase |
| Joint disorders | |
| Rheumatoid arthritis | Cytokine (IL-1), antagonists: others |
| Infectious disorders | |
| AIDS | HIV antigens: cytokines: Thymidine kinase genes; Ribozymes: Rev-M10: others |

After producing the modified vector in step 12, this modified vector is, in one version of the invention, combined with cells from the organism (e.g. human patient, horse, pig, chicken, goat, etc.). It will be appreciated that these cells are the target cells which are isolated from the organism having the disease or illness. These cells may be certain somatic cells of the organism in one embodiment or germ cells in another embodiment or stem cells in yet another embodiment. It will be appreciated that the invention has particular utility in the case of stem cells from various organs of the organism. An example of such a stem cell is the hematopoietic stem cell from the circulatory system of organisms, such as human patients. However, the target cells need not be hematopoietic stem cells or even other types of stem cells. It will be appreciated however that stem cells provide certain advantages over somatic cells in their ability to renew, multiply and differentiate into somatic cells and thereby propagate the effect of the gene therapy such that one gene treatment session (e.g. a single injection of transformed stem cells) is sufficient to "cure" the disease or provide a remedy for at least some of the symptoms of the disease or illness. In one alternative embodiment, cells isolated from a first organism may be transformed according to the EPD procedures of the invention and used to effect gene therapy on a second organism which is typically of the same species as the first organism. Thus, cells from one human may be isolated, combined with a construct and an EPD buffer, transformed with the EPD procedure of the invention and then placed into another human. Thus, the target cells need not come from the organism having the disease or illness but rather from another, typically healthy, organism of the same species.

Figure 1A:
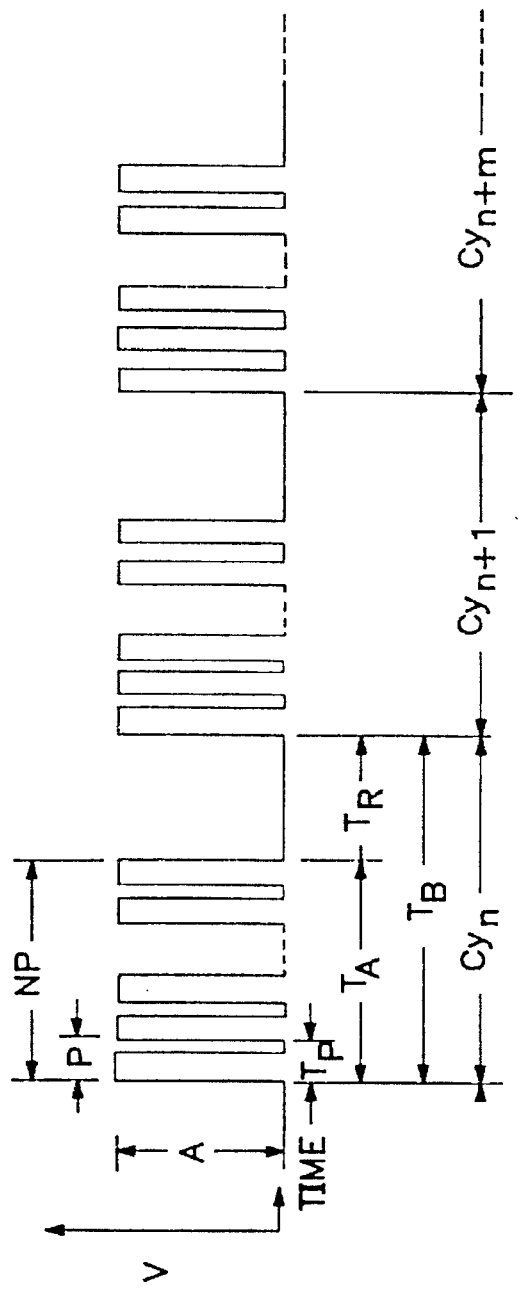
FIG. 1a shows a graph of voltage vs. time for an EPD procedure.
Figure 1A:
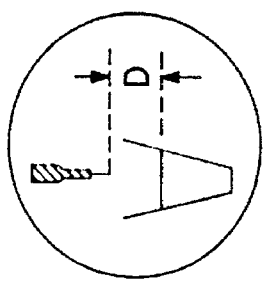

The modified vector is combined with the target cells isolated from the organism in step 14 and this combination is made in an electronic pulse delivery buffer solution. In a typical embodiment, this solution will comprise: a saline solution with salts, amino acids and a buffer for maintaining the pH of the solution. An example of such a buffer is "Iscove's Modified Dulbecco's Media," ("IMDM") which is commercially available from Gibco of Gaithersburg, Md. This buffer is used at its normal 1×concentration as specified by Gibco in its commercially available literature. The modified vector, the target cells and the buffer solution are introduced into the main chamber of a reaction chamber of a reactor used for performing EPD. This reactor typically uses the reaction chambers described herein, although other types of reaction chambers used for EPD may be used. The typical conditions for performing EPD include the creation of an electric field by applying repeatedly, using electronic pulses, a voltage in the range of about 150 to 30,000 volts across two electrodes. These electrodes are typically placed around the reaction chamber's main chamber such that there is a distance of approximately 1.0 mm to 400 mm between the electrodes. The pulses typically have a 50% duty cycle (half on and half off during a particular pulse as shown in FIG. 1a) and last for approximately 1 to 200 microseconds. The pulses are typically applied in a burst of pulses during a cycle where there are a certain number of pulses (NP) during a cycle and a relaxation period with no pulses during the cycle and the cycle is typically repeated. This is shown in more detail in FIG. 1a. The following table also sets out the EPD reaction conditions along with the reaction chamber typically used in the case of certain genetic material and vectors for certain target cells.

TABLE C

| Desired Genetic Material ("Gene") & target cell | Insertional & linearizing Rest. Endos. | Marker Gene (if any) | Plasmid or other vector | EPD Reaction chamber (FIGS. 5–8) & Reaction conditions and buffer |
| --- | --- | --- | --- | --- |
| NGFR gene into T cytotoxic/ suppressor cells (with CD8 + antigen) | Alwn I (linearizing) | None unless NeoR desired | pMP | FIG. 5b reactor, IMDM EPD buffer, 25 KV pulse amplitude, 200 pulses/cycle, 160 μsec pulse time ($T_p$), burst time ($T_B$) of 2.0 sec., 50 cycles, 35 mm diameter cylindrical main chamber (dish about 1.5 cm in height) with about 35 mm diameter plate electrodes, d1 = d2 = 0.5 mm (so effective distance between electrodes is about 1.6 mm). |
| NGFR gene into T cytotoxic/ suppressor cells (with CD8 + antigen) | Alwn I (linearizing) | None unless NeoR desired | pMP | FIG. 6b reactor, IMDM EPD buffer, 6 KV pulse amplitude, 60 pulses per cycle, 160 usec pulse time ($T_P$), burst time ($T_B$) of 0.8 sec., 20 cycles, 35 mm diameter cylindrical main chamber (petri dish about 1.5 cm in height) with tip 606a of electrode about 0.8 cm above top of EPD solution (d = 0.8 cm). |
| NGFR gene into T cytotoxic/ suppressor cells (with CD8 + antigen) | Alwn I (linearizing) | None unless NeoR desired | pMP | FIG. 8b reactor, IMDM EPD buffer, 30 KV pulse amplitude, 300 pulses per cycle, 180 usec pulse time ($T_P$), burst time ($T_B$) of 2 sec., 80 cycles, 35 mm diameter cylindrical main chamber (petridish about 1.5 cm in height) with d = 0.8 cm (distance between top of solution and bottom of electrode 806). |
| NGFR gene into hematopoietic stem cells (with CD34+ | Alwn I (linearizing) | Non unless NeoR desired | pMP | FIG. 5b reactor, IMDM EPD buffer, 25 KV pulse amplitude, 200 pulses/cycle, 160 |

TABLE C-continued

| Desired Genetic Material ("Gene") & target cell | Insertional & linearizing Rest. Endos. | Marker Gene (if any) | Plasmid or other vector | EPD Reaction chamber (FIGS. 5–8) & Reaction conditions and buffer |
|---|---|---|---|---|
| antigen) | | | | μsec pulse time ($T_P$), burst time ($T_B$) of 2.0 sec., 50 cycles, 25 mm diameter cylindrical main chamber (dish about 1.5 cm in height) with about 35 mm diameter plate electrodes, d1 = d2 = 0.5 mm (so effective distance between electrodes is about 1.6 mm). |
| NGFR gene into hematopoietic stem cells (with CD34+ antigen) | Alwn I (linearizing) | Non unless NeoR desired | pMP | FIG. 6b reactor, IMDM EPD buffer, 6 KV pulse amplitude, 60 pulses per cycle, 160 usec pulse time ($T_P$), burst time ($T_B$) of 0.8 sec., 20 cycles, 35 mm dimeter cylindrical main chamber (petri dish about 1.5 cm in height) with tip 606a of electrode about 0.8 cm above top of EPD solution (d = 0.8 cm). |
| NGFR gene into hematopoietic stem cells (with CD34+ antigen) | Alwn I (linearizing) | Non unless NeoR desired | pMP | FIG. 8b reactor, IMDM EPD buffer, 30 KV pulse amplitude, 300 pulses per cycle, 180 usec pulse time ($T_P$), burst time ($T_B$) of 2 sec., 80 cycles, 35 mm diameter cylindrical main chamber (petridish about 1.5 cm in height) with d = 0.8 cm (distance between top of solution and bottom of electrode 806). |
| Human VDR (vitamin D-3 receptor) gene into Human Fibroblast cells | Pvu I (to linearize) EcoRI (to insert) | NeoR or LacZ or None | pGEM-4 | FIG. 5b reactor, DMEM buffer, 30 KV pulse amplitude, 300 pulses/cycle (NP = 300), 140 μsec pulse time ($T_P$), burst time ($T_B$) of 1.5 sec., 50 cycles, 35 mm diameter cylindrical main chamber (dish about 1.1 cm in height) with about 35 mm diameter plate electrodes, and distance between electrodes about 1.2 cm ($d_1$ and $d_2$ = 0.5 mm). |
| Human VDR (vitamin D-3 receptor) gene into Human Fibroblast | Pvu I (to linearize) EcoRI (to insert) | NEOR or LacZ or None | pGEM-4 | FIG. 6b reactor, DMEM buffer, 4 KV pulse amplitude, 200 pulses per cycle, 160 μsec = $T_P$, $T_B$ = 1.2 |

TABLE C-continued

| Desired Genetic Material ("Gene") & target cell | Insertional & linearizing Rest. Endos. | Marker Gene (if any) | Plasmid or other vector | EPD Reaction chamber (FIGS. 5–8) & Reaction conditions and buffer |
|---|---|---|---|---|
| cells | | | | sec., 28 cycles, 35 mm diameter cylindrical main chamber (petri dish about 1.5 cm in height) with tip 606a of electrode about 0.8 cm above top of EPD solution (d = 0.8 cm). |
| Human VDR (vitamin D-3 receptor) gene into Human Fibroblast cells | Pvu I (to linearize) EcoRI (to insert) | NeoR or LacZ or None | pGEM-4 | FIG. 7c reactor, DMEM buffer, 2.5 KV pulse amplitude, 60 pulses per cycle (NP = 60), $T_P = 140$ μsec, $T_B = 2$ sec., 10 cycles, 35 mm diameter cylindrical main chamber (petri dish about 1.5 cm in height) with d = 0.6 cm (distance between top of solution and bottom of electrode 707 ignoring the pins). |
| Human VDR (vitamin D-3 receptor) gene into Human Fibroblast cells | Pvu I (to linearize) EcoRI (to insert) | NeoR or LacZ or None | pGEM-4 | FIG. 8b reactor, DMEM buffer, 28 KV pulse amplitude, NP = 300, $T_P = 170$ μsec, $T_B = 2$ sec., 70 cycles, 35 mm diameter cylindrical main chamber (petri dish about 1.5 cm in height) with d = 0.8 cm (distance between top of solution and bottom of electrode 806). |

Figure 5A:
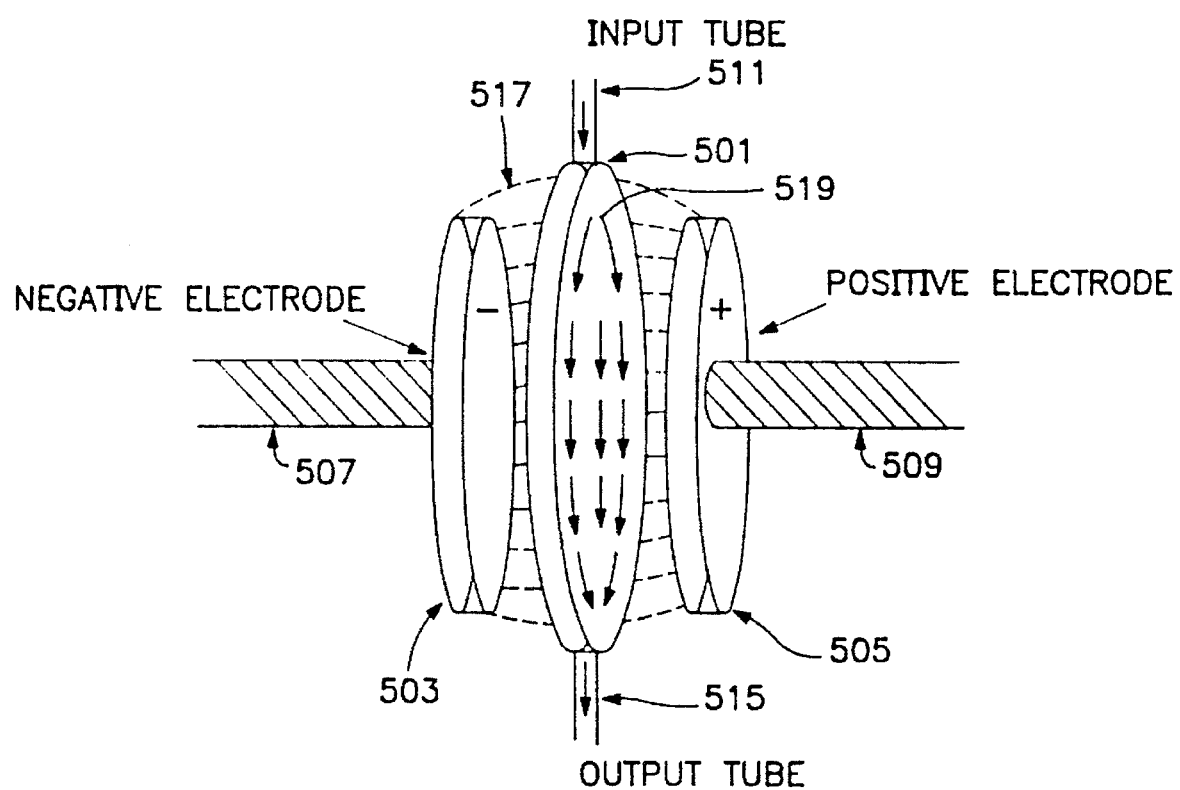
FIG. 5a shows one embodiment of a EPD reaction chamber according to the present invention.

Two of the examples shown in Table C will now be described in further detail. The first example involves the human NGFR gene (Nerve Growth Factor Receptor gene) which is inserted into the genome of the human T cytotoxic/suppressor cells which carry the CD8⁺ antigen. The NGFR gene is inserted into the pMP plasmid with Bluescript backbone, which is commercially available from Stratagene of California. This construct is then lineraized using the restriction endonclease Alwn I, and the resulting lineraized construct is combined with the IMDM EPD buffer and with the target cells, which are T cytotoxic/suppressor cells which possess the CD8 protein antigen on the surface of the cellular membrane of these cells. The combination is then subjected to an EPD procedure of 50 cycles, each cycle 200 pulses per cycle. Each pulse is 160 microseconds long (Tp) (where 80 μsec of this time the voltage across the electrodes is 25 KV and 80 μsec of this time the voltage cross the electrodes is OkV), and the burst time (total time for a cycle including both active pulsing and relaxation time) is 2.0 seconds, thus the total procedure takes about 100 seconds (50 cycles×2 seconds). The voltage amplitude during the pulse when the electrodes are charged is 25 KV (Kilovolts), with a duty cycle of 50% during each pulse. The solution is placed into a reaction chamber such as that shown in FIG. 5b by, for example, a peristaltic pump. In one embodiment, the solution is placed into the chamber and processed, using the above noted EPD procedure, in a batch operation where the solution, with the target cells and the construct carrying the NGFR gene, sits in the main reaction chamber. In another embodiment, the solution is continuously pumped, at a slow rate, through the reaction chamber. In this embodiment which uses continuous pumping, the main chamber shown is FIG. 5c is typically used. The main chamber is typically about the size of a normal 35 mm petri dish having a 35 mm diameter and a height of about 1.5 cm. The electrodes are positioned about 0.5 mm from each face of the dish such that the electrodes are spaced apart from each other by about 1.5 cm with the dish between them. The electrodes do not typically physically or electrically contact the solution, and each electrode is typically disposed opposite to and proximate to a corresponding substantially flat face of the reaction chamber. After completing the EPD procedure described above, the T cytotoxic/suppressor cells, at least a plurality of which having been transferred, are removed from the reaction chamber and then processed further according to the invention. Other examples for the NGFR gene are given in Table C for other reactor chambers.

Another example described in Table C will now be discussed further. In this example, human fibroblast cells are used as the target cell for insertion of the human Vitamin D-3 Receptor (VDR) then into the genome of the target cells. The human VDR gene is inserted into the pGEM-4 plasmid, which is commercially available, to create a modified genetic vector or construct, and the construct is linearized and placed in the DMEM buffer (Dulbecco's Modified Eagle Medium, which is commercially available from Gibco) with the target cells. This combination, in the DMEM buffer solution, is placed in the main chamber of the reactor show in FIG. 5b in order to perform an EPD procedure to thereby transform many of the fibroblast cells. The EPD procedure in this case involves 50 cycles, each cycle having 300 pulses. Each pulse is 140 microseconds long ($T_p=140$ μsec), where 70 μsec of this time the voltage across the electrodes is 30 KV and 70 μsec of this time the voltage is 0kV. The burst time (total time for a cycle including both active pulsing and relaxation time) is 1.5 seconds, giving a total procedure time of about 75 seconds. The voltage amplitude during the pulse when the electrodes are charged is 30 kV. The solution may be placed in the reaction chamber by a peristaltic pump or by gravity feed or other pumps. As with the example given above, the solution may be continuously sent through the chamber or may be processed in batch fashion. The main chamber is typically about the size of a normal 35 mm petri dish having a 35 mm diameter and a height of about 1.0 cm. The electrodes are positioned about 0.5 mm from each face of the dish such that the electrodes are spaced apart from each other by about 1.2 cm with the dish between them. The electrodes do not typically physically or electrically contact the solution, and each electrode is typically disposed opposite to and proximate to a corresponding substantially flat face of the main chamber. After completing the EPD procedure descried above, the human fibroblast cells, at least a plurality of which have been transformed, are removed from the main chamber and then processed further according to the present invention.

After performing EPD, the transformed target cells may be "selected" using conventional tissuing culturing techniques. This is illustrated in the case of stem cells which are target cells in FIG. 2. A typical implementation would be the use of a marker gene such as the NeoR neomycin resistance gene which has been inserted into the vector along with the desired gene. The marker gene expresses a gene product which confers resistance to the transformed target cells so that only transformed target cells grow in a tissue culture medium containing neomycin.

It will be appreciated that this step of selecting transformed target cells is not essential after a gene therapy protocol has been validated through a prior genetic analysis of the transformed cells such as DNA probe testing or other analysis of the genome of the target cells to verify that they have been transformed with the insertion of the desired gene into the genome of the target cells. An example of such a validation for the NGFR gene in the T cytotoxic/suppressor cells is described below. Therefore, step 18 may be omitted in the case of an established (validated) gene therapy protocol and consequently the marker gene need not be inserted into the vector in this type of protocol; that this, only the desired gene without the marker gene is inserted into the vector to produce a modified vector which does not contain the marker gene.

After the transformed target cells have been selected, it may be desirable to further culture the transformed target cells, such as transformed stem cells as noted in step 20 of FIG. 2. This may be useful if the transformed stem cells can multiply in tissue culture in order to increase the number of these cells so that the therapy is more effective for the organism. It will be appreciated that this step 20 may also be omitted if the transformed target cells can provide an adequate remedy for the disease or illness without increasing their numbers. In step 22, the transformed target cells, such as transformed stem cells, or the developed progeny cells from the transformed stem cells may be used for gene therapy. This typically involves placing the transformed target cells (e.g. transformed stem cells) back into the organism (or perhaps another organism of the same species or different species) in order to effect the gene therapy. Typically, this placement will occur by placing the transformed stem cells into the organism, such as by injecting the transformed target cells into a circulatory system of the organism or a particular organ of the organism. Alternatively, the transformed target cells may be placed into the organism by implanting these cells; for example this implantation would be performed in the case of transformed human fibroblast cells. In doing so, the transformed target cell will typically produce a protein or other expression of the desired gene which will result in a cure or partial remedy of the disease or illness. It may be appreciated that further such injections or implantations may be required particularly if somatic cells, rather than stem cells, are used to create the transformed target cells. It will be appreciated that alternate approaches to the therapy may involve the continued culturing of the transformed target cells and the harvesting from this culture of the expressed gene product which is then injected or otherwise placed into the organism; however, this is not usually as desirable as placing the transformed target cells back into the organism.

It will be appreciated that there are numerous ways to verify the insertion of the gene or genetic material into the transformed target cells or into the genome of the transformed target cells. For example, the protocol described above for the NGFR gene and the T cytotoxic/suppressor cells has been verified by fluorescent labeling of transformed target cells. In this example, the procedures described above for inserting the NGFR gene and the pMP plasmid into T cytotoxic/suppressor cells (the target cells) were followed. A control experiment was also performed, where the NGFR gene/pMP construct was combined with the T cytotoxic/suppressor cells in the IMDM EPD solution; this control solution was not subjected to the EPD procedure while the test sample (also containing the NGFR gene/pMP construct and T cytotoxic suppressor cells in the IMDM EPD solution) was subjected to the EPD procedure described above (in the Reaction chamber of FIG. 5b). Both the control sample and the test sample were cultured, separately, and a mouse monoclonal antibody to the Nerve Growth Factor Receptor was added to both the test sample and the control sample. After incubating both samples and washing them with PBS (phosphate buffered saline) a goat anti-mouse antibody (which was fluorescently labeled with FITC) was added to both samples. After incubating both samples, and washing them with PBS, both samples were observed with a light microscope set-up for fluorescent microscopy. The control sample (where EPD was not performed) showed T cytotoxic/suppressor cells in culture without any fluorescence while the test sample (where EPD was performed as described above in the reactor of FIG. 5b) showed fluorescence appearing on the cell membranes of the T cytotoxic cells in culture. This demonstrated that the NGFR gene/pMP construct had been successfully inserted into the target cells, the T cytotoxic suppressor cells, and that the NGFR gene was expressing its gene product, the nerve growth factor receptor which had become a constituent of the cellular membrane of the transformed target cells.

A more specific example of the present invention will now be given while referring to FIGS. 3 and 3a along with FIG. 4. As shown in step 30, the G1Na plasmid is obtained, and the desired gene is inserted into the plasmid to create a modified plasmid. In the case of an established gene protocol (that is, a gene therapy procedure according to the present invention where the gene has been verified to be integrated functionally into the transformed target cells or into the genome of the transformed target cells of the organism) there is no need to include a gene marker, such as the NeoR marker gene into the plasmid. After the desired gene is inserted into the plasmid, the plasmid is linearized to produce a modified linearized plasmid in step 34. This is shown diagramatically in FIG. 4 where the plasmid 55 is first opened at restriction site 56 to insert the desired gene 59 such that the modified plasmid 55a will have two restriction sites 56a and 56b which are identical to the single, unique restriction site 56 found in the plasmid 55. Restriction site 58, which is also a unique restriction site in plasmid 55 and 55a is then used to linearize plasmid 55 to create a linearized modified plasmid 55a. It will be appreciated that exonucleases are typically used during the linearization process after the restriction endonucleases have cleaved the modified plasmid 55a at restriction site 58.

Figure 3:
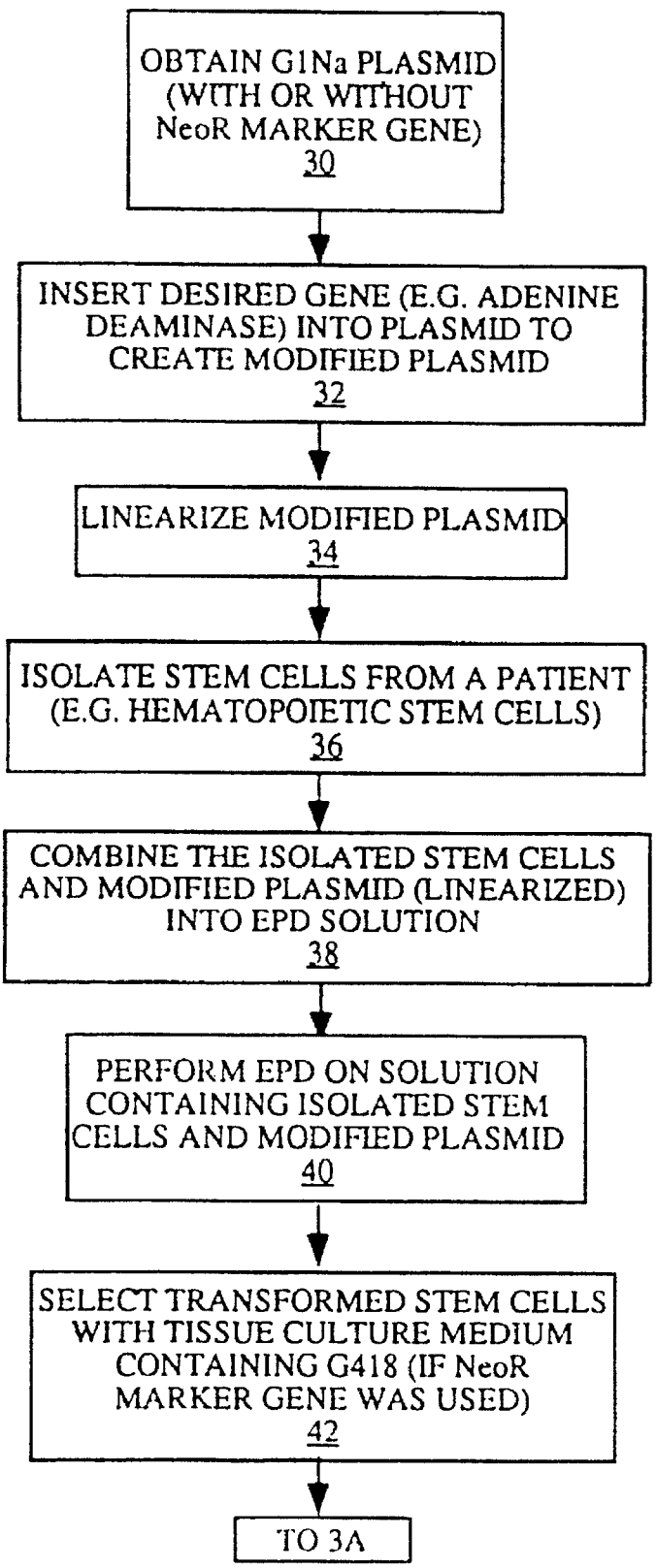
FIG. 3 shows in more detail another example of the process of the present invention.
Figure 3A:
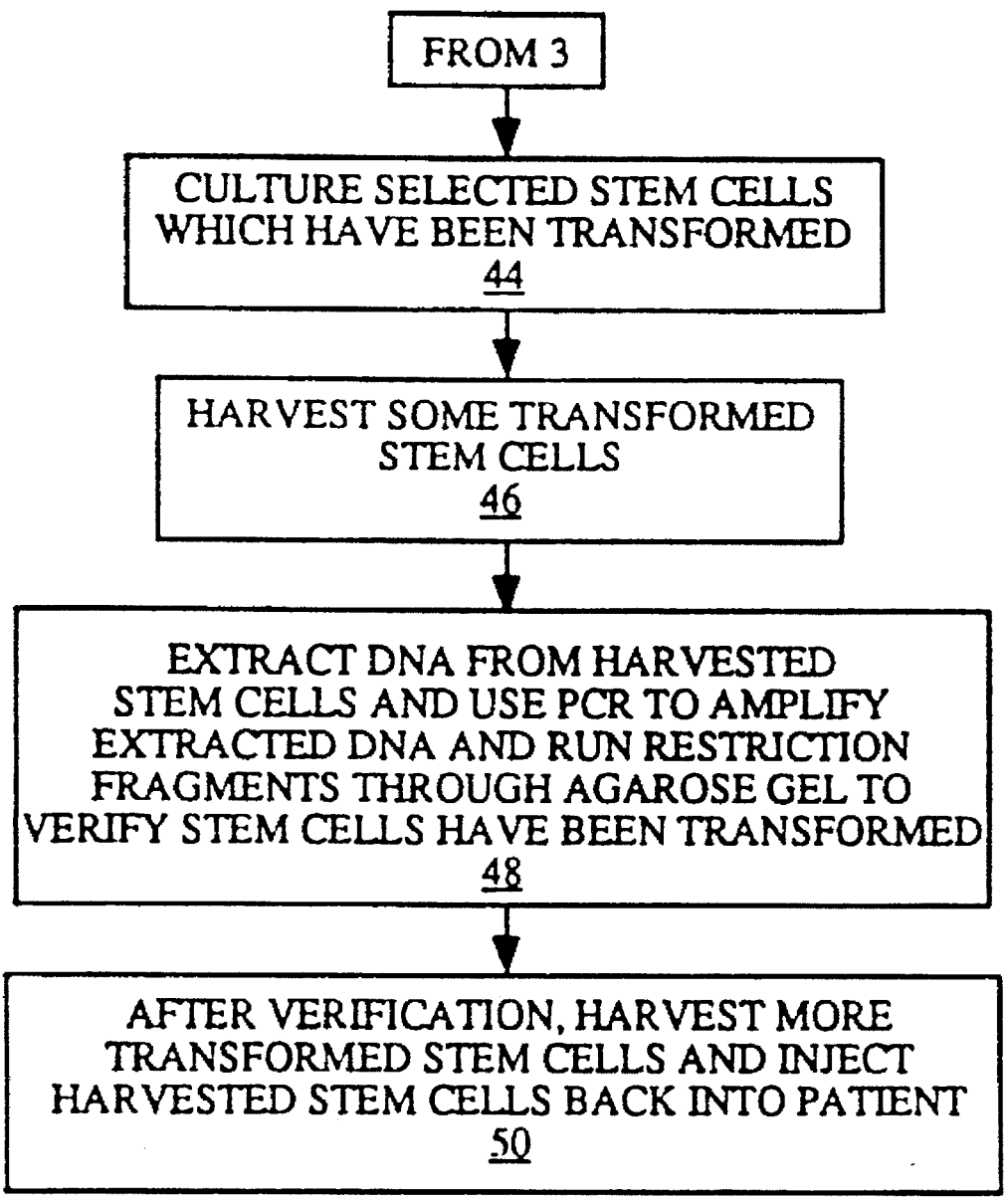
Figure 4:
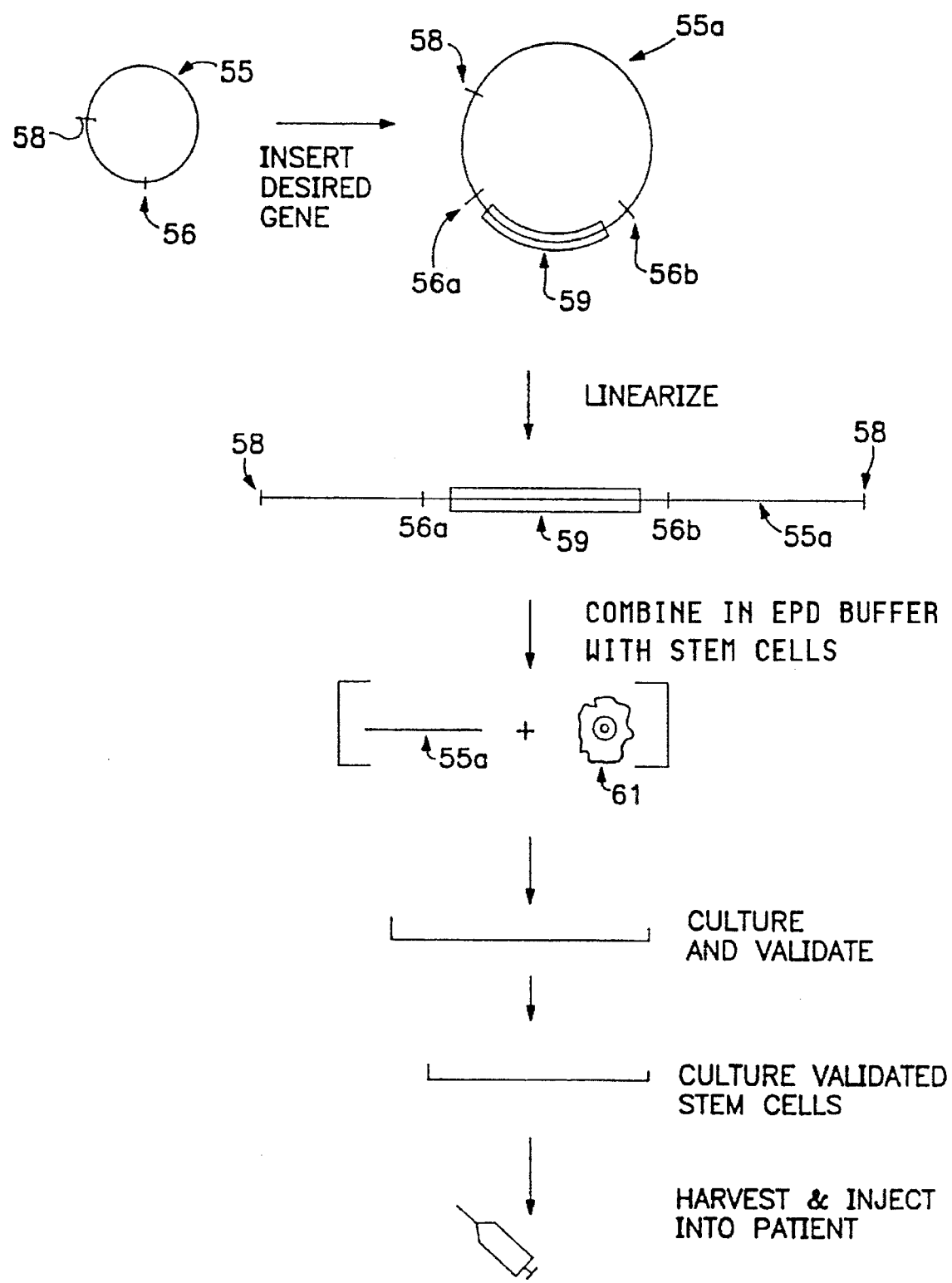
FIG. 4 illustrates certain aspects of an example of the present invention.

Step 36 of FIG. 3 illustrates the isolation process which is typically required in the case of stem cells from a patient. This isolation is usually required due to the relative rarity of stem cells. Numerous techniques are known for isolating stem cells such that a relatively abundant supply of stem cells may be obtained. For example, in the case of the hematopoietic stem cell (sometimes referred to as a pluripotent hematopoietic stem cell), they may be isolated by the use of the CD 34$^+$ antibody to the CD 34 protein on the surface of the cellular membrane of the hematopoietic stem cell. For example, magnetic beads coated with the CD 34$^+$ antibody may be mixed with tissue samples or blood samples from a patient, and the stem cells will remain stuck to the magnetic beads while nonstem cells may be washed away. There are also known columns, such as the Ceprate LC column (from CellPro. Inc. of Oregon) which uses a similar approach with this antibody. In each case, an enzyme such as chymopapain may be used to separate the stem cells from the magnetic beads or from the column after washing away the nonstem cells. Alternatively, cell sorters such as that described in U.S. Pat. No. 5,150,313 may be utilized to separate hematopoietic stem cells from other cells of a patient, whether the sample is taken from bone marrow tissue or from the circulatory system of the organism or from human umbilical cord blood.

The stem cells are then combined with the modified plasmid in a EPD solution. This is shown in FIG. 4 where the modified plasmid 55a which has been linearized is combined with stem cells, such as the stem cell 61 in a EPD buffer. The combination is then placed in a main chamber of a reaction chamber of a EPD reactor and EPD procedures are then performed on the combination in order to cause the transfer of the desired gene into the genome of the stem cells, such as the hematopoietic stem cells. This is shown diagramatically in step 40 of FIG. 3. If a marker gene was used so that selection of the transformed cells in a tissue culture may be performed, then step 42 is performed in order to select the transformed hematopoietic stem cells from the non transformed stem cells. As shown in step 42, if the NeoR marker gene was used, then a tissue culture medium containing G418 is used to sustain only the growth of the transformed stem cells and those stem cells which have not been transformed by the EPD process will not be sustained and will die. It will be appreciated that this selection step of step 42 is not necessary in the case of an established gene protocol of the present invention and thus would not be used in a gene therapy procedure which has been established; similarly, the marker gene would not be inserted into the plasmid to produce a modified plasmid. FIG. 4 shows such a case where no marker gene is used and only the desired gene is inserted into the plasmid 55 to produce the modified plasmid 55a. As noted above, in such a circumstance, the step of selecting transformed cells such as step 42 is not performed, although it still may be prudent to validate the transfer of the desired gene into the genome of the stem cells as described below and as is shown in FIG. 4.

If the stem cells have been selected in step 42, then these selected stem cells are further cultured in step 44. If no selection has occurred because step 42 has been omitted, then the transformed stem cells are cultured and some of the cells are harvested in step 46. The harvest cells are tested to validate the transformation in step 48. This is also shown in FIG. 4 where after the EPD process, the stem cells are cultured and some of the cultured stem cells are harvested in order to validate the transformation of the stem cells. The process of step 48 involves the use of known procedures to verify the integration of the genetic material/gene, such as desired gene 59 of FIG. 4, into the genome of the stem cells to thereby transform the stem cells. As shown in FIG. 3a, this may involve using PCR technology to amplify extracted DNA from the harvested stem cells and then preparing restriction fragments which are then run in an electric field through an agarose gel (gel electrophoresis) with known restriction fragments from a desired gene in order to verify/validate that the gene has been properly integrated into the genome of the hematopoietic stem cells. Other techniques for verifying the integration of the genetic material into the genome of the stem cells will be appreciated by those in the art. For example, a fragment of the desired gene 59 may be used as probe with Southern Blotting techniques to establish that the construct has been integrated into the genome of the stem cells. Alternatively, a known antibody to the gene product expressed by the gene under normal circumstances may be used to determine whether the gene product is present in the transformed stem cells or in the tissue culture media in which the stem cells grow. After verification/validation that the stem cells have been transformed, more transformed stem cells are harvested from the culture and then injected into the patient to cause the gene therapy to occur.

The various improved reactors and their corresponding reaction chambers will now be described while referring to FIGS. 5a, 5b, 5c, 6a, 6b, 7a, 7b, 7c, 8a and 8b. FIG. 5a shows a reaction chamber in an EPD reactor. The reaction chamber includes a main chamber 501, a negative electrode 503, and a positive electrode 505. There is an input tube 511 which is coupled to an input port of the main chamber 501 and an output tube 515 which is coupled to an output port to the main chamber 501. The combination of the target cells and the EPD buffer and genetic material is introduced into the main chamber 501 via the input tube 511 and exits the main chamber 501 through the output tube 515 after the process of performing EPD on the combination. The electronic pulses are applied to the negative and positive electrodes 503 and 505 respectively via wires 507 and 509 and these pulses create periodically an electric field 517. As can be seen from FIG. 5a, the main chamber includes a first and second substantially flat face or surface, and each of the electrodes 503 and 505 include a substantially flat face. The surface area of the first and second faces of the main chamber is substantially equivalent to the surface area of the face of the substantially flat plate electrode. This is shown in FIG. 5a. This surface area of the electrode may be smaller or larger than the surface area of the corresponding face of the main chamber. As shown in FIG. 5a, one substantially flat face of the chamber 501 is opposite to and proximate to electrode 503, and the other substantially flat face of the main chamber is opposite to and proximate to the substantially flat fact of electrode 505. It will be appreciated that the substantially flat face may be slightly rounded to have a slightly concave surface or cross section. For example, the electrode 806 (FIG. 8b) may be used in place of the electrode 505 while still using the electrode 503 or both electrodes 503 and 505 may be replaced with electrodes having the shape of electrode 806.

It can be seen from FIG. 5a that both electrodes are isolated physically and electrically from the solution containing the construct and the target cells which are to be transformed. This is contrary to conventional wisdom which utilizes electrodes where at least one of these electrodes is in direct contact with the solution. It would be appreciated that both electrodes or merely one electrode may be mounted on a shaft which may be moved relative to the main chamber in order to change the distance between the electrode's face and the corresponding face of the main chamber. For example, referring to FIG. 5b, if the electrodes 503a and 505a are mounted on a shaft which can be moved relative to the main chamber 501a, then the distance is $d_1$ and $d_2$ can be varied. Typically, $d_1$ and $d_2$ are varied in a range from 0.1 mm to about 2 mm in the case of the reaction chamber shown in FIG. 5b.

Figure 5B:
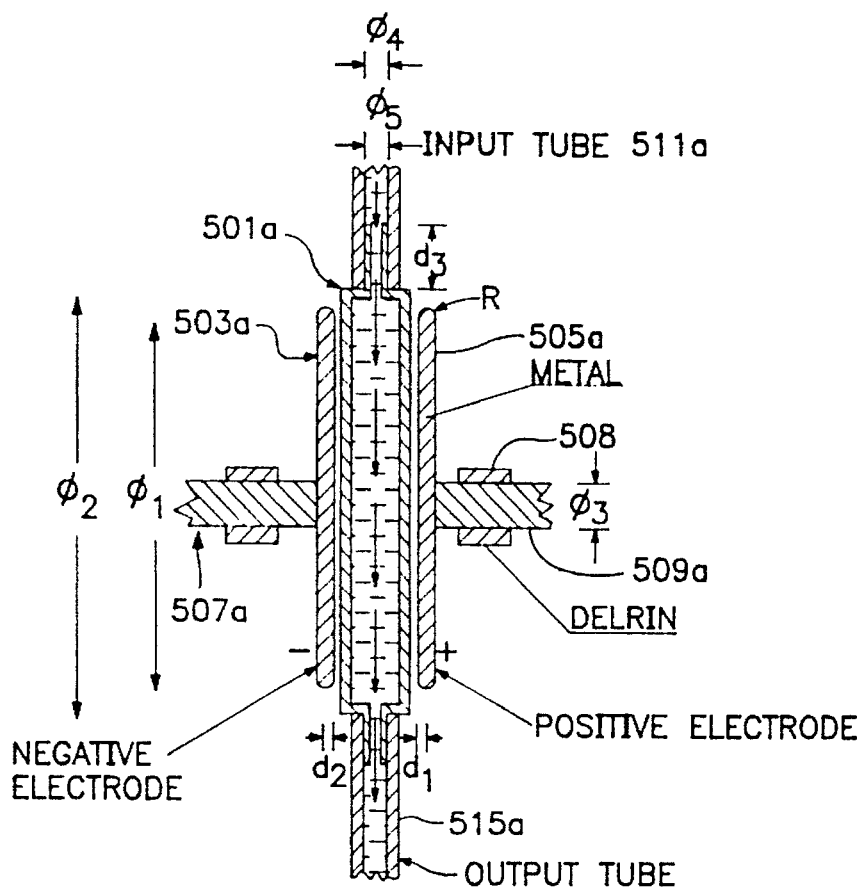
FIGS. 5b and 5c show further aspects of this embodiment.
Figure 5C:
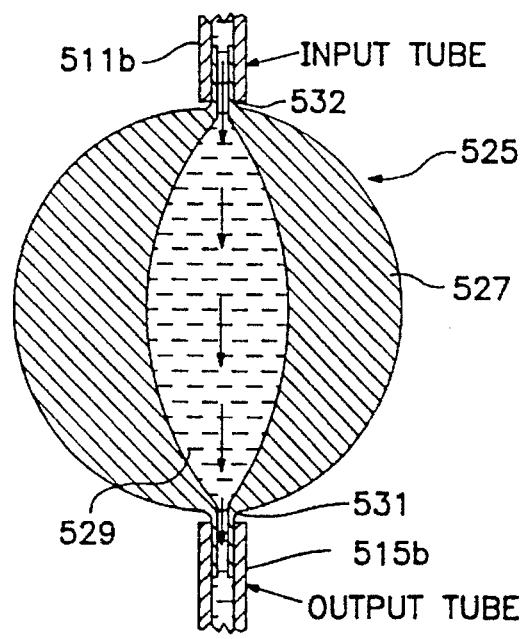

FIG. 5b shows a particular example of the reactor chamber of FIG. 5a. The sample solution is inserted into the main chamber 501a through the input tube 511a. After the EPD procedure has been performed on the sample solution, the sample solution exists the main chamber 501a through the output tube 515a. The reaction chamber of FIG. 5b may be used in either batch mode or continuous processing mode. In batch mode, a sample is placed into the reactor's main chamber 501a and no flow occurs through the main chamber during the EPD procedure. This is typically accomplished by sealing at least the output tube 511a. In a continuous process, the sample solution may be fed through the main chamber 501a using the peristaltic pump or gravity feed at a slow rate.

It will be appreciated that sterility will need to be maintained before and during the EPD procedure so that the transformed cells may be placed into an organism. The main chamber 501a is shaped substantially like a petri dish; a typical example would be a 35 mm diameter petri dish having a height of approximately 1 cm, except that the dish cannot be separated as is possible with a normal petri dish. FIG. 5c shows a particular embodiment of a main chamber which may be used in place of the main chamber of 501a. The main chamber 525 of FIG. 5c has a hollow region 529 and a filled region 527 such that the test solution can only flow through the hollow region 529 of the main chamber 525. This main chamber 525 is typically made out of a plastic material which is similar to the plastic material used to make plastic petri dishes, and the resulting structure is sterilized along with the input and output tubes. The resulting structure (a sterilized combination of main chamber 525 and its input and output tubes) may then be packaged in a sterile environment and used for an EPD procedure to transform target cells for use in a gene therapy procedure. The main chamber 525 includes an extended lip 531 and an extended lip 532 which are used to engage the input tubes 515b and 511b respectively. It can be seen by comparing FIG. 5a and 5c that the test solution will flow only through the hollow region 529 in FIG. 5c while in the embodiment shown in FIG. 5a the test solution may flow as shown by the flow arrows 519 through the entire cavity of chamber 501.

Figure 6A:
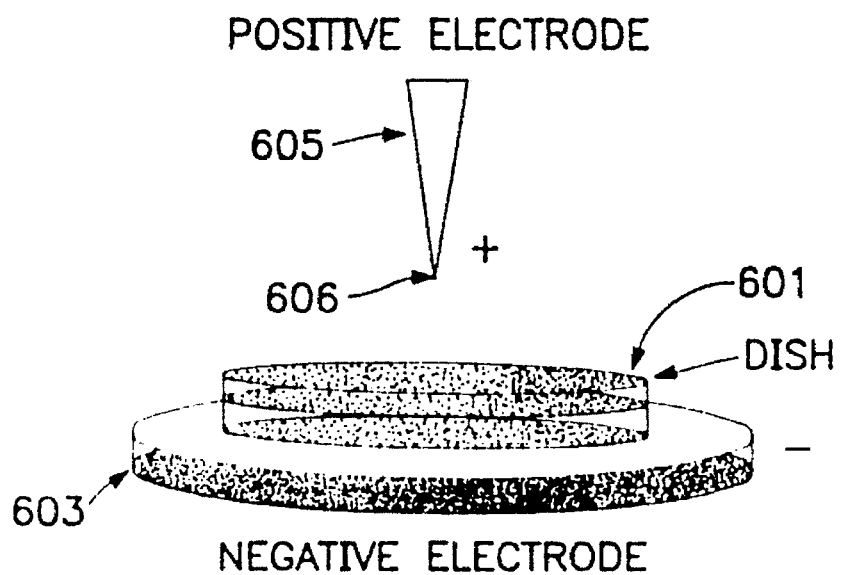
FIG. 6a shows another embodiment of an EPD reaction chamber according to the present invention.
Figure 6B:
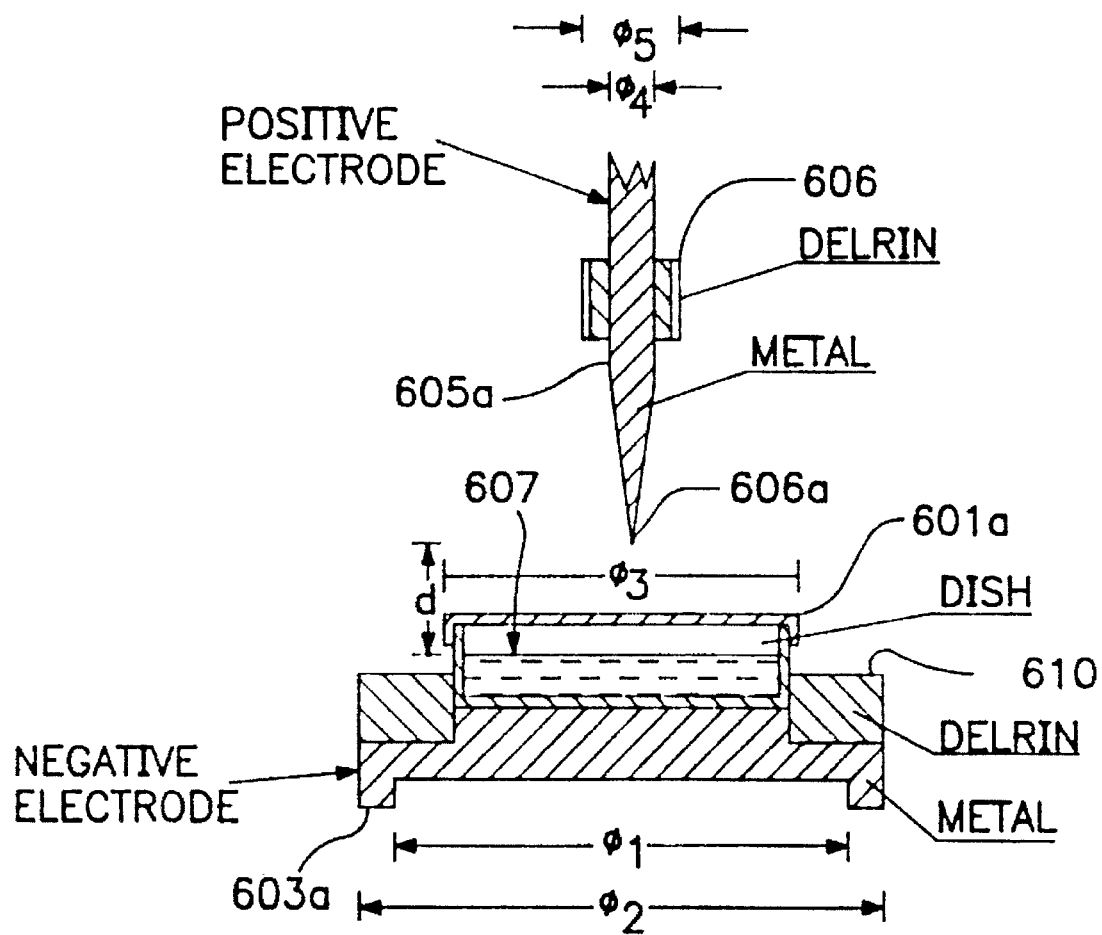

FIG. 6a shows another embodiment of a reaction chamber in a reactor according to the present invention. The positive electrode 605 includes a relatively sharp tip 606 that is disposed above the dish 601 which contains the combination of the target cells, the genetic material and the EPD buffer. Underneath the dish 601 is a negative electrode 603. The tip 606 is placed in close proximity to the top of the dish 601 which may be a conventional petri dish. An EPD generator is coupled to the two electrodes 605 and 603 to generate electronic pulses which thereby create an electric field, although the shape of the field generated by the electrode 605 and electrode 603 is different than the field 517 shown in FIG. 5 due to the shapes of the electrodes. As with the embodiment shown in FIGS. 5a and 5b, the positioning of the electrode 605 relative to the top of the dish 601 may be controlled by various mechanical mechanisms. For example, the electrode 605 may have a screw shaft at one end opposite to the tip 606, and this screw shaft engages a gear which may be rotated in order to raise or lower the electrode 605 in order to control the distance between the tip of the electrode and top of the solution 607. As shown in FIG. 6b, this distance, d, is typically set to be between 0.1 mm and 2 cm.

As shown in FIG. 6b, the dish 601a may be a conventional sterile petri dish which contains the test solution which comprises the modified genetic vector, the target cells and the EPD buffer. The dish may be stabilized on the electrode 603a by plastic insulative ring 610 which is disposed above the electrode 603a. An insulative support 606 may be used to position the electrode 605a above the top of the solution 607.

Figure 7A:
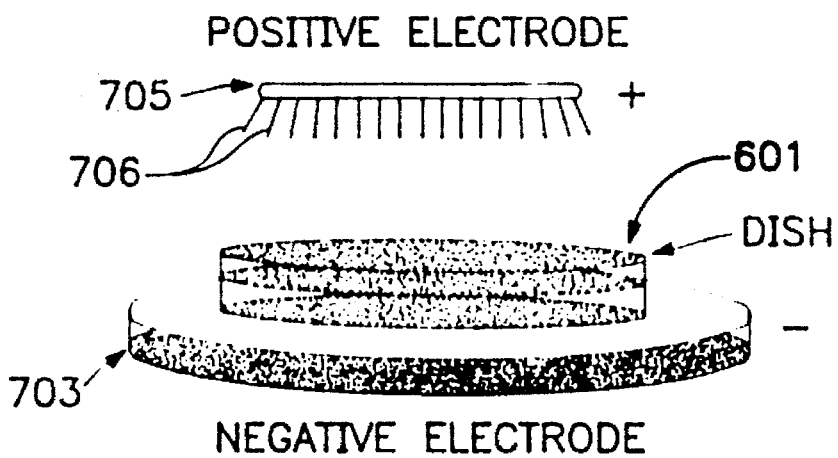
FIG. 7a shows another embodiment of an EPD reaction chamber according to another embodiment of the present invention.
Figure 7B:
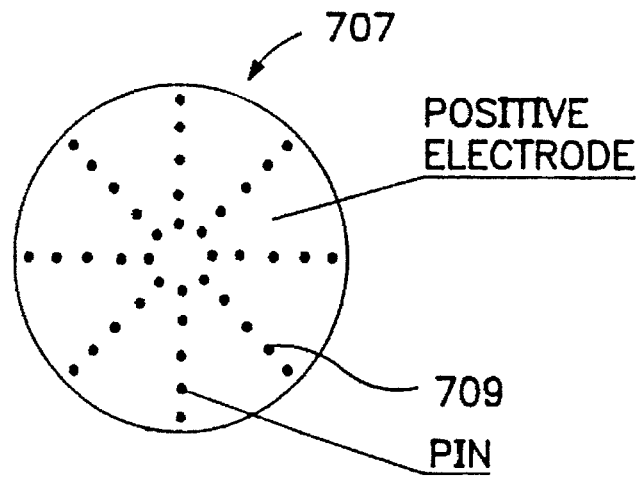
Figure 7C:
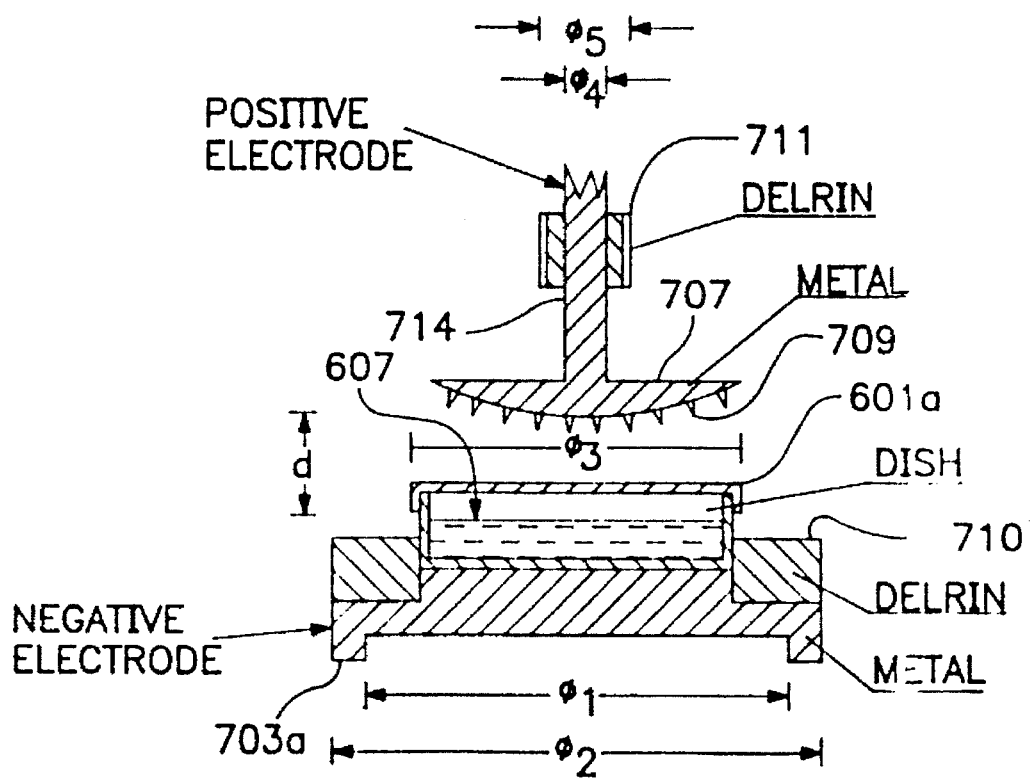

FIG. 7 shows another embodiment of a reaction chamber in a EPD reactor according to the present invention. The dish 601 is disposed above a negative electrode 703, and above the dish 601 is the positive electrode 605 having metallic pins 706. FIGS. 7b and 7c show an alternative embodiment of the reactor of FIG. 7a. In this embodiment, the positive electrode has a curved face which is still substantially flat; this curved face faces the top of the solution 607 such that the distance between the bottom of the electrode 707 and the top of the solution 607 is designated by the distance measurement d. This distance is typically about 1 cm (ignoring the fact that the pins are actually a bit closer to the top of the solution 607). These pins are typically about 1 mm—2 mm long. FIG. 7b shows the electrode 607 as it appears from the top of the solution 607. As can be seen from FIG. 7b, the electrode 707 has a plurality of pins 709 protruding from the surface of the electrode 707. As with the other embodiments described above, the dish 601a may be a conventional sterile petri dish containing the construct and the target cells in an EPD buffer solution. The dish 601a may be held from the top of the electrode 703a by a plastic insulating ring 710. As with the other embodiments described above, the electrode 707 is mounted on a mechanism which allows the distance d to be varied. In this embodiment d is set to be typically in the range of 0.1 mm to 2 mm.

Figure 8A:
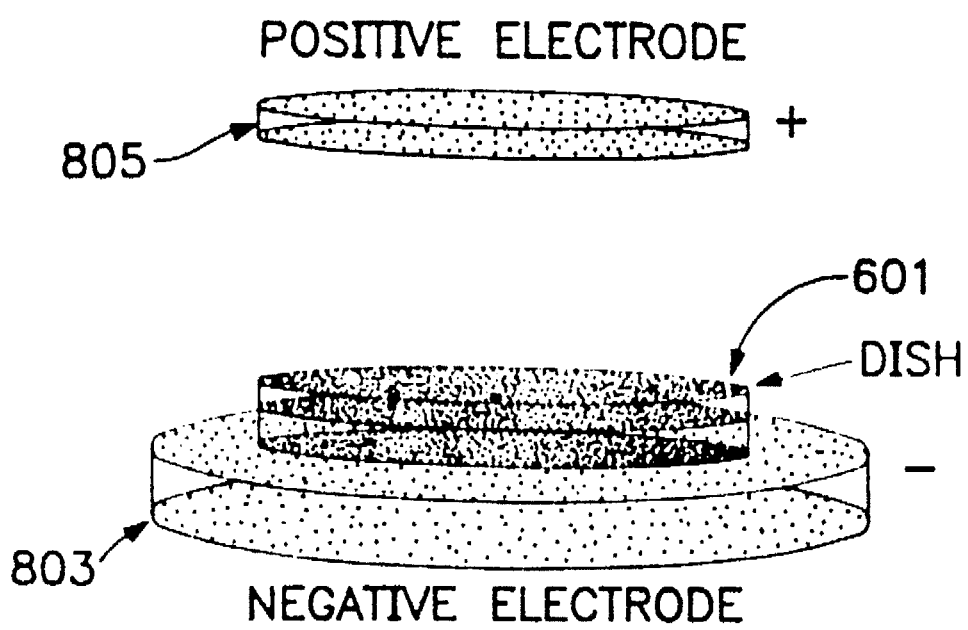
FIG. 8a shows another EPD reaction chamber according to an embodiment of the present invention.
Figure 8B:
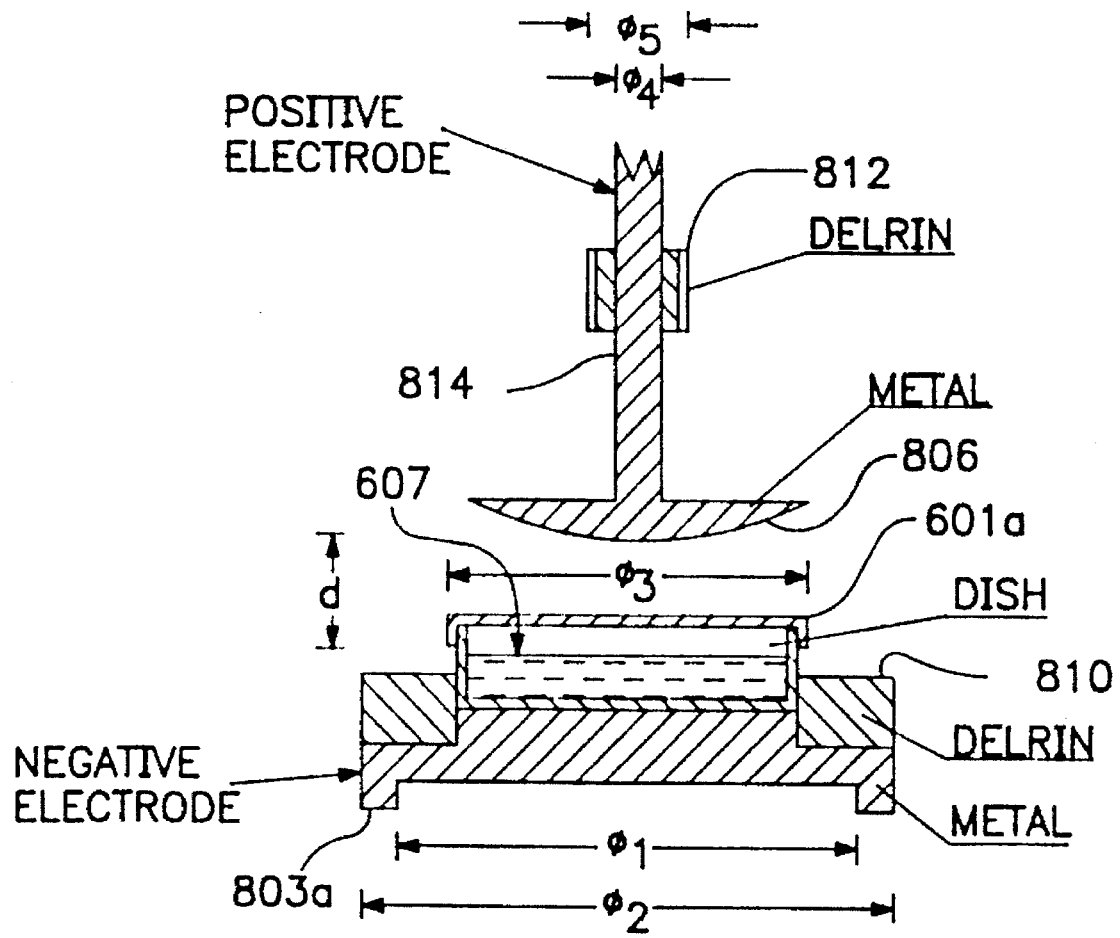

FIG. 8a shows an alternative embodiment of a reaction chamber in an EPD reactor according to the present invention. The dish 601 is disposed above and proximate to a negative electrode 803. Above the dish 601 is a positive electrode 805. The dish 601 includes a first and second substantially flat surface, where one flat surface is proximate to and opposite to one electrode, such as electrode 803 and the other face of dish 601 is proximate to and opposite to the other electrode. A further alternative embodiment of a reactor according to the present invention is shown in FIG. 8b. In this embodiment, the positive electrode 806 has a slightly curved face which faces the top of the solution 607 which may be contained in the conventional, sterile petri dish 601a. The electrode 806 has a shaft 814, which may be supported by an insulating ring 812. Typically, the shaft 814 is mounted to a mechanism which allows the height, shown by the distance d, of the electrode above the top of the solution 607 to be varied. The dish 601a is mounted securely to the electrode 803a by an insulating ring 810 which may snugly hold the dish 601a. The distance d, between the electrode 806 and the top of the solution 607 may be set in a range from 0.1 mm to 2 mm and is typically about 1 cm.

It will be appreciated that in each of the reaction chambers described above, the electrodes, which are typically metal electrodes are both physically and electrically isolated from the solution such that they do not contact the solution and do not directly allow the conduction of current into the solution as in the prior art. Thus, as in shown in FIG. 8b, the electrode 806 has a substantially flat surface which is above the solution 607 but does not contact that solution. Similarly, the electrode 803a does not contact the solution as the plastic bottom wall of the dish 601a prevents the electrode 803a from contacting the solution 607.

FIGS. 9 and 10 illustrate construct maps of various constructs of combinations of genetic material and vectors which may be utilized with the present invention. FIG. 9 shows the plasmid pMP which includes the interleukin-2 gene inserted with an LTR (Long Terminal Repeat). FIG. 10 shows another construct made from the plasmid pCMVRv plasmid. This construct includes the gene for the surface protein M10 from HIV virus and also includes the promoter region labeled CMV from the cytomegalovirus and the Neo marker gene.

The specific examples given to describe the present invention are intended to illustrate various possible embodiments of the present invention without limiting the generality of the invention. Various modifications of the invention in addition to these shown and described herein will become apparent to those skilled it the art from the foregoing description and fall within the scope of the following claims.

I claim:

1. A reaction chamber for introducing nucleic acids into cells, said reaction chamber comprising:

a main chamber having a substantially flat face, said main chamber holding a combination of a nucleic acid, a plurality of cells and an electronic pulse delivery solution; and a first electrode having a second substantially flat face which is disposed opposite to and proximate to said first substantially flat face, said first electrode being coulped to recieve electronic pulses to perform electronic pulse delivery of said nucleic acid into at least some of said plurality of cells, said first electrode being physically isolated from said solution.

2. A reaction chamber for introducing nucleic acids into cells, said reaction chamber comprising:

a main chamber, said main chamber holding a combination of a nucleic acid, a plurality of cells and an electronic pulse delivery solution; and a first electrode and a second electrode, said first and said second electrodes being coulped to recieve electronic pulses to perform electronic pulse delivery of said nucleic acid into at least some of said plurality of cells, said first and said second electrodes being physically and electrically isolated from said solution such that said electrodes do not contact said solution.

3. A reaction chamber as in claim 2 wherein said reaction chamber is used for the processing of cells wherein said cells will contain an expression vector comprising a nucleotide sequence encoding a gene product of interest and wherein said cells are capable of producing said gene product of interest at a detectable level.

4. A reaction chamber as in claim 2 wherein said main chamber includes a first substantially flat face and said first electrode has a second substantially flat face which is disposed opposite to and proximate to said first substantially flat face.

* * * * *